United States Patent [19]
Okabe et al.

[11] Patent Number: 5,589,192
[45] Date of Patent: Dec. 31, 1996

[54] GEL PHARMACEUTICAL FORMULATION FOR LOCAL ANESTHESIA

[75] Inventors: Hideaki Okabe; Eiji Suzuki, both of Urawa; Masao Kogure, Saitama-ken; Takanori Saito, Misato, all of Japan

[73] Assignee: Lintec Corporation, Tokyo, Japan

[21] Appl. No.: 353,322

[22] Filed: Dec. 5, 1994

[30]  Foreign Application Priority Data

Dec. 3, 1993 [JP] Japan .................. 5-339439

[51] Int. Cl.$^6$ .................................. A61L 15/00
[52] U.S. Cl. .................. 424/486; 424/443; 424/445; 424/449; 514/816; 514/818; 514/944; 514/946
[58] Field of Search .................... 424/402, 443, 424/445, 484, 486, 449, 487; 514/816, 818, 887, 944, 946, 947

[56]  References Cited

U.S. PATENT DOCUMENTS

| | | | |
|---|---|---|---|
| 3,598,122 | 8/1971 | Zaffaroni | 128/268 |
| 4,885,161 | 12/1989 | Cornell | 424/78 |
| 4,931,279 | 6/1990 | Bawa | 424/427 |
| 5,064,652 | 11/1991 | Bay | 424/445 |
| 5,419,913 | 5/1995 | Podell et al. | 424/448 |

FOREIGN PATENT DOCUMENTS 4-305523  10/1992  Japan .

*Primary Examiner*—Thurman K. Page
*Assistant Examiner*—Sharon Howard
*Attorney, Agent, or Firm*—Millen, White, Zelano & Branigan, P.C.

[57]  ABSTRACT

An article of manufacture in the form of a gel pharmaceutical formulation for local anesthesia is prepared by a process comprising: coating a supporting substrate, which preferably is porous, e.g., a non-woven fabric, and has an impervious backing sheet, with a matrix of a copolymer of alkyl (meth)acrylates and (meth)acrylic acid and a local anesthetic whereby the matrix penetrates the substrate, crosslinking the copolymer in the matrix to form a polymer/drug matrix, and coating the surface of the matrix with an aqueous fluid, thereby converting the matrix into a gel and preferably covering the gel matrix with an impervious protective sheet. The product has excellent percutaneous absorption, provides local anesthesia easily just by attaching the formulation to the skin, enables elimination of various kinds of pain, such as the pain at the time of hypodermic injection, can be removed easily from the skin, and causes no soiling of fingers, hands or cloths.

25 Claims, 1 Drawing Sheet

GEL PHARMACEUTICAL FORMULATION FOR LOCAL ANESTHESIA

BACKGROUND OF THE INVENTION

1. Field of the Invention

The present invention relates to an article of manufacture, in the form of a novel gel pharmaceutical formulation adapted for local anesthesia. More particularly, the present invention relates to a gel pharmaceutical formulation for local anesthesia which has excellent percutaneous absorption, provides local anesthesia easily merely by applying the formulation to the skin, enables elimination of various kinds of pain, such as the pain at the time of injection, can be removed easily from the skin, and causes no soiling of fingers, hands or cloths.

2. Description of the Related Art

Heretofore, in simple situations, such as saturation of a wound, and for injection with a relatively large syringe, subcutaneous injection of a local anesthetic is conducted as a preliminary treatment. Also in some hospitals, a cream or a gel ointment containing a local anesthetic is used as ODT (Occlusive Dressing Technique) when a surgical operation is necessary in a wide range.

However, the pain at the time of penetration of the injection needle cannot be avoided by the subcutaneous injection technique. Creams and ointments for local anesthesia have drawbacks in that pharmaceuticals cannot be applied quantitatively and their removal after the application without causing soiling of hands, fingers and cloths is not easy.

As the local anesthetic, xylidine compounds such as lidocaine, bupibacaine, mepibacaine, and the like, and aminobenzoic acid compounds, such as procaine, tetracaine, and the like, are known. These compounds in base form or as the salt of hydrochloric acid are widely used for the surface anesthesia in dental areas, for local anesthesia, verteba anesthesia, epidural anesthesia, and the like.

By making use of the local anesthetic effect of a local anesthetic, an externally attached pharmaceutical formulation containing lidocaine has been proposed for curing, for example, neuralgia in herpes zoster and neuralgia after herpes zoster (Japanese Patent Application Laid Open No. Heisei 4(1992)-305523). However, the externally attached pharmaceutical formulation has a drawback in that a long time (about 4 to 8 hours) is required for exhibiting the local anesthetic effect after the pharmaceutical formulation is attached to the skin because the lidocaine content is as low as 1 to 10% by weight.

SUMMARY OF THE INVENTION

The present invention accordingly has an object to provide as an article of manufacture an externally attached pharmaceutical formulation for local anesthesia which enables elimination of various kinds of pain, such as pain at the time of injection, which can be removed easily from the skin, and which causes no soiling of fingers, hands or cloths.

Extensive studies were undertaken by the present inventors to develop the externally attached pharmaceutical formulation having the desirable properties described above. In the studies, attention was paid to the fact that the percutaneous absorption of a drug increases in proportion to the partition coefficient of the drug between the skin and a matrix containing the drug, the diffusion coefficient of the drug in the skin, and the concentration of the drug in the matrix. As the result of the studies, it was discovered that, when a process comprising mixing a local anesthetic with a (meth)acrylic copolymer, coating the mixture on a supporting substrate, and forming the combined material into a gel after crosslinking is used, the local anesthetic is effectively kept in the matrix in a high concentration, and that a gel pharmaceutical formulation showing excellent percutaneous absorption can be obtained by the process described above. The present invention has been completed on the basis of the discovery.

Thus, the present invention provides a gel pharmaceutical formulation for local anesthesia prepared by a process comprising: coating and thereby impregnating a supporting substrate with a mixture containing a copolymer of alkyl (meth)acrylates and (meth)acrylic acid and a local anesthetic, crosslinking the copolymer in the mixture to form a polymer/drug matrix and coating the surface of the polymer/drug matrix with an aqueous fluid, thereby converting the coated polymer/drug matrix into a gel. Other and further objects, features and advantages of the invention will appear more fully from the following description.

BRIEF DESCRIPTION OF THE DRAWINGS

The invention will be described with reference to the accompanying drawing, wherein.

Figure 1:
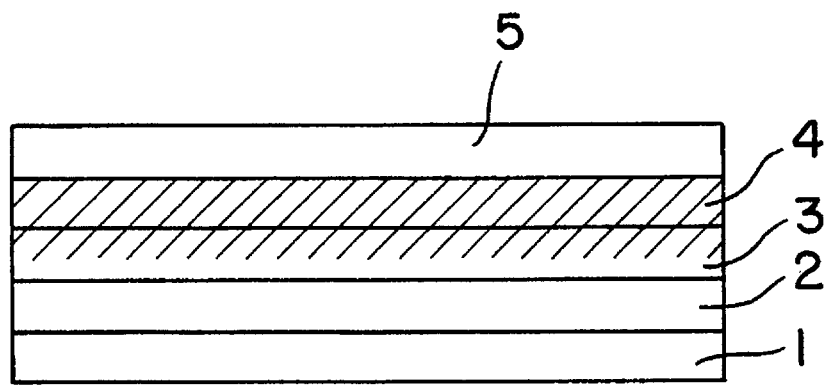
FIG. 1 shows the structure of an example of the gel pharmaceutical formulation for local anesthesia of the present invention.

The numbers in the figure have the meanings as listed in the following:

1: a substrate having the barrier property

2: a layer of an adhesive

3: a porous material impregnated with a gel polymer/drug matrix

4: a layer of a gel polymer/drug matrix

5: a release film

DETAILED DESCRIPTION OF THE INVENTION

In the gel pharmaceutical formulation of the present invention, a copolymer of alkyl (meth)acrylates and (meth)acrylic acid is used as a vehicle. Examples of the alkyl (meth)acrylate used as a material monomer of the copolymer include methyl (meth)acrylate, ethyl (meth)acrylate, propyl (meth)acrylate, butyl (meth)acrylate, amyl (meth)acrylate, hexyl (meth)acrylate, cyclohexyl (meth)acrylate, 2-ethylhexyl (meth)acrylate, isooctyl (meth)acrylate, nonyl (meth)acrylate, and the like. The alkyl (meth)acrylate may be used singly or as a combination of two or more kinds. As the comonomer used in combination with the alkyl (meth)acrylates, (meth)acrylic acid is used.

In the copolymer, other monomers copolymerizable with the alkyl (meth)acrylates and (meth)acrylic acid are suitably used in combination with the alkyl (meth)acrylates and (meth)acrylic acid, if necessary. Examples of the other copolymerizable monomer include: polymerizable unsaturated compounds containing hydroxyl group, such as 2-hydroxyethyl (meth)acrylate, 2-hydroxypropyl (meth)acrylate, 3-hydroxypropyl (meth)acrylate, 2-hydroxybutyl (meth)acrylate, 3-hydroxybutyl (meth)acrylate, 4-hydroxybutyl (meth)acrylate, and the like; polymerizable unsaturated compounds containing amino group, such as 2-aminoethyl (meth)acrylate, 2-aminopropyl (meth)acrylate, 3-aminopropyl (meth)acrylate, 2-aminobutyl (meth)acrylate, 3-aminobutyl (meth)acrylate, 4-aminobutyl (meth)acrylate, and the like; polymerizable compounds containing vinyl group, such as vinyl methyl ether, vinyl ethyl ether, vinyl propyl ether, vinyl butyl ether, vinylpyrrolidone, and the like; and polymerizable unsaturated compounds containing carboxylic group, such as maleic acid, fumaric acid, itaconic acid, anhydrides of these acids, and the like. The copolymerizable monomer may be used singly or as a combination of two or more kinds.

In the copolymer used in the present invention, it is preferred that at least 50% by weight of the alkyl (meth) acrylate units are alkyl (meth)acrylate units in which the alkyl group has 1 to 3 carbon atoms. It is also preferred that the ratio by weight of alkyl (meth)acrylate units to (meth) acrylic acid units is in the range of 95:5 to 70:30.

A copolymer of an alkyl acrylate, a hydroxyalkyl acrylate, and acrylic acid is particularly preferable as the copolymer.

The process for preparing the copolymer of alkyl (meth) acrylates and acrylic acid described above is not particularly limited. For example, radical solution polymerization can be favorably adopted. More specifically, alkyl (meth) acrylates and (meth)acrylic acid are dissolved in a suitable organic solvent together with other copolymerizable monomers, if necessary, in amounts specified for each component. A polymerization initiator is added to the solution and the polymerization is conducted at a temperature preferably in the range of 50° to 80° C. for 5 to 40 hours. Thus, a solution containing the desired copolymer can be obtained. As the polymerization initiator in this process, polymerization initiators conventionally used in radical polymerization, such as organic peroxides like benzoyl peroxide and cumene peroxide, and azo compounds like 2,2'-azobisisobutyronitrile, can be used.

As the anesthetic in the gel of the present invention, for example, xylidine compounds, such as lidocaine, bupibacaine, mepibacaine, and the like, and aminobenzoic acid compounds, such as procaine, tetracaine, and the like, can be used. The effect of the present invention can be best exhibited by using lidocaine. The compound described above may be used in the isolated form or as the salt of hydrochloric acid. The compound described above may be used singly or as a combination of two or more kinds. The anesthetic is mixed with the copolymer of alkyl (meth)acrylates and (meth)acrylic acid to form a polymer/drug matrix. The amount of the anesthetic mixed can be selected in the range of 1 to 60% by weight based on the total amount of the copolymer and the anesthetic. An amount in the range of 15 to 60% by weight is preferable for exhibiting the effect of anesthesia more quickly and for stability of the gel formulation.

The following is an example of a process for preparing the gel pharmaceutical formulation for local anesthesia of the present invention.

To the solution containing the copolymer of alkyl (meth) acrylates and (meth)acrylic acid obtained as described above, the local anesthetic is added in the amount described above. A crosslinking agent, such as a polyfunctional isocyanate, a polyfunctional epoxy compound, and the like, is added to the solution in a suitable amount and the solution for the coating is prepared. It is advantageous that the concentration of the copolymer in the solution is in the range of 10 to 50% by weight. A percutaneous absorption enhancer may be added, if necessary. Examples of the percutaneous absorption enhancer include limonene, menthol, salicylic acid, hyaluronic acid, oleic acid, N,N-diethyl-m-toluamide, n-butyl stearate, benzyl alcohol, isopropyl myristate, isopropyl palmitate, polypropylene glycol, crotamitone, diethyl sebacate, N-methylpyrrolidone, N-ethylpyrrolidone, lauryl alcohol, ethanol, and the like. An antiseptic and an antioxidant may also be added, if desired. Furthermore, ethanolamine, diethanolamine, triethanolamine, and the like, may be added for increasing thermodynamic activity of the pharmaceutical in the matrix, improving distribution to the skin and enhancing absorption into the skin. When an antiseptic or an antioxidant is used, attention must be paid to the effect of the antiseptic or the antioxidant on the function to control discharge of the drug and on irritation to the skin.

The solution thus prepared is coated onto a supporting substrate in such a manner that the dried amount of the coated material is generally in the range of 10 to 200 g/m². The coated solution is dried and crosslinked simultaneously at a temperature in the range of 60° to 120° C. and a polymer/local anesthetic matrix is prepared. The matrix thus prepared is coated with an aqueous fluid in an amount of 50 to 200 parts by weight based on 100 parts by weight of the matrix by using a Mayer bar, a spray, a gravure, or the like. The matrix coated with, and thus impregnated, with, the aqueous fluid, is formed into a gel. Thus, the gel pharmaceutical formulation for local anesthesia of the present invention is obtained.

Examples of the aqueous fluid used for the formation of the gel polymer/drug matrix described above include water and solutions of water containing ethanol, propylene glycol, glycerol, polyethylene glycol, or the like. Water-soluble agents selected from the percutaneous absorption enhancer described above may be contained in the aqueous fluid, if desired.

As the supporting substrate, a substrate comprising a composite material which comprises a porous material laminated to a material having the barrier property to water, drugs, and additives is preferable. When a material having the barrier property to water, drug, and additives is used alone without lamination of a porous material, the copolymer of alkyl (meth)acrylates and (meth)acrylic acid is occasionally peeled off by swelling (increase in the volume) of the copolymer in the process of the formation of the gel. In contrast, when the material having the barrier property is laminated with a porous material and the solution for coating is coated on the surface of and thus impregnates the porous material and the laminate is then dried, the copolymer and the porous material become entangled so that the copolymer is not peeled off in the process of the formation of the gel and during a storage period.

The material having the barrier property and the porous material may be laminated by using an adhesive, by heat sealing, or by other methods. The method of lamination is not particularly limited. Examples of the material having the barrier property include sheets and films of synthetic resins, such as polyesters, polyvinyl chloride, polyethylene, polyurethane, and the like. Examples of the porous material include non-woven, woven, knit, and the like.

To the gel pharmaceutical formulation for local anesthesia of the present invention thus obtained, a release film may be laminated. In this case, the release film is removed at the time of application of gel pharmaceutical formulation.

The gel pharmaceutical formulation for local anesthesia of the present invention shows excellent percutaneous absorption and the effect of local anesthesia can be exhibited merely by attaching the formulation to the skin.

FIG. 1 shows the structure of an example of the gel pharmaceutical device for local anesthesia of the present invention. In the supporting substrate, the porous material 3 is laminated to the material having the barrier property 1 with the layer of an adhesive 2. The gel material layer 4 is formed on the porous material 3 of the supporting substrate. The shaded area shows entanglement of the gel matrix in the porous material. The release film 5 is laminated further on top of the layer of the gel matrix 4.

To summarize the advantages obtained by the invention, the gel pharmaceutical formulation for local anesthesia of the present invention shows excellent percutaneous absorption, provides local anesthesia easily just by attaching the formulation to the skin, enables elimination of various kinds of pain, such as the pain at the time of injection, can be removed easily from the skin, and causes no soiling of fingers, hands or cloths.

The invention will be understood more readily with reference to the following examples; however, these examples are intended to illustrate the invention and are not to be construed to limit the scope of the invention.

A pharmaceutical formulation for local anesthesia was evaluated according to the following methods.

(1) Amount of the percutaneous absorption (concentration of a drug in the skin)

Hairs at the abdominal part of a male Wistar rat (160 to 180 g) were removed by using an animal clipper. A pharmaceutical preparation was attached to the skin at the part where hairs had been removed. After one hour, the skin was taken out and homogenized. Amount of the drug in the skin was determined by the high performance liquid chromatography.

(2) Separation of crystals of a drug

One week after the pharmaceutical formulation was made, crystallinity of a drug in the gel formulation was observed visually and evaluated according to the following criterion:

○: No separation of crystals
Δ: partial separation of crystals
x: overall separation of crystals (3) Clinical evaluation of local anesthesia A pharmaceutical formulation was attached to the inner side of a lower arm of a person. The formulation was peeled off after 0.5, 1, 1.5, 2, or 3 hours. The treated part was pricked with a needle and pain felt by the pricking was evaluated by the following criterion:

○: no pain felt
Δ: slight pain felt
x: pain felt

PREPARATION EXAMPLE 1

Into a mixed solvent comprising 50 g of ethyl acetate and 100 g of methyl ethyl ketone, 50 g of ethyl acrylate, 30 g of methyl acrylate, 18 g of acrylic acid, and 2 g of 2-hydroxyethyl acrylate were dissolved and 0.1% by mol of 2,2'-azobisisobutyronitrile based on the total of the monomers was added to the mixed solution. The mixture was polymerized in the nitrogen atmosphere at 60° C. for 10 hours and a solution of acrylic polymer A for preparation of a gel pharmaceutical formulation was obtained.

PREPARATION EXAMPLE 2

Into a mixed solvent of 50 g of ethyl acetate and 100 g of methyl ethyl ketone, 50 g of ethyl acrylate, 40 g of methyl acrylate, 8 g of acrylic acid, and 2 g of 2-hydroxyethyl acrylate were dissolved and a solution of acrylic polymer B was prepared by the same method as that in Preparation Example 1.

PREPARATION EXAMPLE 3

Into a mixed solvent of 50 g of ethyl acetate and 100 g of methyl ethyl ketone, 50 g of ethyl acrylate, 20 g of methyl acrylate, 28 g of acrylic acid, and 2 g of 2-hydroxyethyl acrylate were dissolved and a solution of acrylic polymer C was prepared by the same method as that in Preparation Example 1.

PREPARATION EXAMPLE 4

A solution of acrylic polymer D was prepared according to the same method as that in Preparation Example 1 except that propyl acrylate was used in place of ethyl acrylate in Preparation Example 1.

PREPARATION EXAMPLE 5

A solution of acrylic polymer E was prepared according to the same method as that in Preparation Example 1 except that 2-hydroxyethyl acrylate was used in place of acrylic acid in Preparation Example 1.

PREPARATION EXAMPLE 6

A solution of an acrylic adhesive material [the unit of butyl acrylate: the unit of acrylic acid=95:5 by weight] was coated on a polyester film of 25 μm thickness in such an amount that dried thickness of the film is 20 μm. After the coated material was dried, the coated film was laminated with a non-woven fabric having a unit weight of 30 g/m$^2$ and a supporting substrate was prepared.

EXAMPLE 1

To 100 g of the solution of acrylic polymer A, 40 g of lidocaine and 0.1 g of a polyfunctional isocyanate [a product of Nippon Polyurethane Co., Ltd.; trade name, Coronate L] were added. The mixture was coated on the surface of the non-woven fabric of the supporting substrate prepared in Preparation Example 6 in such a manner that a coating which impregnated the substrate was applied thereto in an amount after drying of 50 g/m$^2$. The coated laminate was dried at 100° C. and crosslinked. Then, onto the surface coated with the polymer/lidocaine matrix thus obtained, a 50% by weight aqueous solution of ethanol was coated with a Mayer bar in an amount of 50 g/m$^2$. On the layer thus coated, a polyester film of 38 μm thickness which had been treated with the release treatment on one surface was laminated and a gel pharmaceutical formulation for local anesthesia was prepared. Results of the evaluation are shown in Table 2.

EXAMPLES 2 TO 17

Gel pharmaceutical formulations were prepared according to the same method as that in Example 1 except that kind of the polymer solution, kind and amount of the local anesthetic added to the polymer solution, kind and amount of the percutaneous absorption enhancer added to the polymer solution or aqueous solution,, and kind and amount of the aqueous fluid used for the formation of gel were as shown in Table 1. Results of the evaluation are shown in Table 2.

TABLE 1

| | polymer | | local anesthetic and percutaneous absorption enhancer added to the polymer solution | | aqueous fluid used for the formation of gel | |
|---|---|---|---|---|---|---|
| | kind | amount (g/m²) | kind | amount (g/m²) | kind | amount (g/m²) |
| Example 1 | A | 25 | lidocaine | 25 | 50% by wt. aq. soln. of ethanol | 50 |
| Example 2 | A | 33.3 | lidocaine | 16.7 | 50% by wt. aq. soln. of ethanol | 50 |
| Example 3 | A | 25 | lidocaine | 25 | 30% by wt. aq. soln. of ethanol | 50 |
| Example 4 | A | 25 | lidocaine | 25 | water | 50 |
| Example 5 | A | 25 | lidocaine | 25 | water | 70 |
| Example 6 | A | 25 | lidocaine | 25 | water | 100 |
| Example 7 | A | 25 | lidocaine | 25 | 30% by wt. aq. soln. of propylene glycol | 50 |
| Example 8 | A | 25 | lidocaine | 25 | 30% by wt. aq. soln. of glycerol | 50 |
| Example 9 | A | 25 | lidocaine | 25 | 30% by wt. aq. soln. of polyethylene glycol 600 | 50 |
| Example 10 | A | 25 | lidocaine | 25 | 50% by wt. aq. soln. of ethanol | 100 |
| Example 11 | B | 25 | lidocaine | 25 | 50% by wt. aq. soln. of ethanol | 50 |
| Example 12 | C | 25 | lidocaine | 25 | 50% by wt. aq. soln. of ethanol | 50 |
| Example 13 | D | 25 | lidocaine | 25 | 50% by wt. aq. soln. of ethanol | 50 |
| Example 14 | A | 22.2 | lidocaine isopropyl myristate | 22.2 5.6 | 50% by wt. aq. soln. of ethanol | 50 |
| Example 15 | A | 25 | lidocaine | 25 | aq. soln. contg. 50% by wt. of ethanol and 1% by wt. of limonene | 50 |
| Example 16 | A | 25 | lidocaine | 25 | aq. soln. contg. 50% by wt. of ethanol and 2% by wt. of menthol | 50 |
| Example 17 | A | 20 | lidocaine procaine | 20 10 | 50% by wt. aq. soln. of ethanol | 50 |

COMPARATIVE EXAMPLE 1

A gel pharmaceutical formulation was prepared according to the same process as that in Example 1 except that the solution of acrylic polymer E was used in place of the solution of acrylic polymer A in Example 1. Results of the evaluation are shown in Table 2.

COMPARATIVE EXAMPLE 2

Into 150 g of ethyl acetate, 93 g of butyl acrylate, 5 g of acrylic acid, and 2 g of 2-hydroxyethyl acrylate were dissolved. Then, 0.1% by mol of 2,2'-azobisisobutyronitrile based on the total amount of the monomers was added to the solution. Polymerization was conducted in a nitrogen atmosphere at 60° C. for 10 hours and an adhesive solution was obtained. To 100 g of the adhesive solution, 40 g of lidocaine and 0.1 g of a polyfunctional isocyanate [a product of Nippon Polyurethane Co., Ltd.; trade name, Coronate L] were added. The mixture was coated on a polyester film of 25 μm thickness in such a manner that the dried amount of the coating is 50 g/m². The coated film was dried at 100° C. and crosslinked. Then, a polyester film of 38 μm thickness which had been treated with a release agent on one surface was laminated to the coated film and a gel pharmaceutical formulation for local anesthesia in the tape form was prepared. Results of the evaluation are shown in Table 2.

COMPARATIVE EXAMPLE 3

A gel pharmaceutical formulation for local anesthesia in tape form was prepared according to the same process as that of Comparative Example 2 except that 20 g of lidocaine was used in place of the 40 g of lidocaine used in Comparative Example 2. Results of the evaluation are shown in Table 2.

COMPARATIVE EXAMPLE 4

Into 150 g of ethyl acetate, 88 g of butyl acrylate, 10 g of acrylic acid, and 2 g of 2-hydroxyethyl acrylate were dissolved and a solution of an adhesive material and a pharmaceutical formulation in tape form were prepared according to the same method as that in Comparative Example 2. Results of the evaluation are shown in Table 2.

COMPARATIVE EXAMPLE 5

A pharmaceutical formulation for local anesthesia in tape form was prepared according to the same method as that in Comparative Example 4 except that 20 g of lidocaine was used in place of 40 g of lidocaine in Comparative Example 4. Results of the evaluation are shown in Table 2.

TABLE 2

| | conc. of pharmaceutical in the skin (μg/g skin) | separation of crystals | degree of local anesthesia after the specified time (hr) | | | | |
|---|---|---|---|---|---|---|---|
| | | | 0.5 | 1 | 1.5 | 2 | 3 |
| Example 1 | 2800 | o | x | o | o | o | o |
| Example 2 | 1290 | o | x | x | o | o | o |
| Example 3 | 2260 | o | x | o | o | o | o |
| Example 4 | 2050 | o | x | o | o | o | o |
| Example 5 | 2170 | o | x | o | o | o | o |
| Example 6 | 2320 | o | x | o | o | o | o |
| Example 7 | 1920 | o | x | Δ | o | o | o |
| Example 8 | 1890 | o | x | Δ | o | o | o |
| Example 9 | 1750 | o | x | Δ | o | o | o |
| Example 10 | 2460 | o | x | o | o | o | o |
| Example 11 | 2150 | o | x | o | o | o | o |
| Example 12 | 2330 | o | x | o | o | o | o |
| Example 13 | 2720 | o | x | o | o | o | o |
| Example 14 | 3560 | o | Δ | o | o | o | o |
| Example 15 | 3120 | o | x | o | o | o | o |
| Example 16 | 3010 | o | x | o | o | o | o |
| Example 17 | — | o | Δ | o | o | o | o |
| Comparative Example 1 | — | o | — | — | — | — | — |
| Comparative Example 2 | 950 | x | x | x | x | x | o |
| Comparative Example 3 | 620 | Δ | x | x | x | Δ | o |
| Comparative Example 4 | 1080 | x | x | x | x | x | o |
| Comparative Example 5 | 390 | 0 | x | x | x | Δ | o |

The product of Comparative Example 1 had almost no adhesive ability and evaluation of the amount of the percutaneous absorption and the degree of the local anesthesia achieved was not possible. In Comparative Examples 2 and 4, the pharmaceutical formulations showed large amounts of crystals and could not be used practically to achieve local anesthesia. The results in Table 2 clearly show that the gel pharmaceutical formulations of the present invention exhibited percutaneous absorption and local anesthesia superior to the pharmaceutical formulations of the Comparative Examples.

What is claimed is:

1. A pharmaceutical article comprising: a supporting substrate having on a surface thereof an aqueous gel coating consisting essentially of a local anesthetic and a gelled crosslinked copolymer of alkyl (meth)acrylate and (meth)acrylic acid, which impregnates the substrate, which article is produced by forming a polymer/drug matrix of the local anesthetic and an uncrosslinked copolymer corresponding to the crosslinked copolymer, applying a coating of the polymer/drug matrix and crosslinking agent for the copolymer to a surface of the substrate to impregnate the substrate therewith, crosslinking the copolymer in the coating to form the crosslinked copolymer, and contacting the surface of the coating with an aqueous fluid, thereby converting the coating into a gel.

2. A pharmaceutical article according to claim 1, wherein at least 50% by weight of the alkyl (meth)acrylate units in the copolymer are alkyl (meth)acrylate in which the alkyl group has 1 to 3 carbon atoms.

3. A pharmaceutical article according to claim 1, wherein the weight ratio of the alkyl (meth)acrylate units to (meth)acrylic acid units in the copolymer is 95:5 to 70:30.

4. A pharmaceutical article according to claim 2, wherein the weight ratio of the alkyl (meth)acrylate units to (meth)acrylic acid units in the copolymer is 95:5 to 70:30.

5. A pharmaceutical article according to claim 1, wherein the copolymer is a copolymer of an alkyl acrylate, a hydroxyalkyl acrylate, and acrylic acid.

6. A pharmaceutical article according to claim 4, wherein the copolymer is a copolymer of an alkyl acrylate, a hydroxyalkyl acrylate, and acrylic acid.

7. A pharmaceutical article according to claim 1, wherein the local anesthetic content in the aqueous gel coating is 15 to 60% by weight based on the combined weight of the anesthetic and copolymer.

8. A pharmaceutical article according to claim 1, wherein the local anesthetic is lidocaine.

9. A pharmaceutical article according to claim 1, wherein the local anesthetic is procaine.

10. A pharmaceutical article according to claim 1, wherein the supporting substrate is a composite material comprising a porous material laminated to a backing material which is impervious to the contents in the gel.

11. A pharmaceutical article according to claim 1, wherein the aqueous fluid is water.

12. A pharmaceutical article according to claim 1, wherein the aqueous fluid is aqueous ethanol.

13. A pharmaceutical article according to claim 1, wherein the substrate is porous.

14. A pharmaceutical article according to claim 1, wherein the substrate is a nonwoven fabric.

15. A pharmaceutical article according to claim 1, wherein the surface of the substrate opposite the surface to which the polymer/drug matrix coating is applied is covered by an impervious backing sheet.

16. A pharmaceutical article according to claim 1, wherein the surface of the substrate to which the polymer/drug matrix coating is applied is covered by an impervious protective sheet.

17. A pharmaceutical article according to claim 1, wherein the copolymer is a copolymer of an alkyl acrylate, a hydroxyalkyl acrylate, and acrylic acid in which at least 50% by weight of the alkyl (meth)acrylate units in the copolymer are alkyl (meth)acrylate units in which the alkyl group has 1 to 3 carbon atoms; wherein the weight ratio of the alkyl (meth)acrylate units to (meth)acrylic acid units in the copolymer is 95:5 to 70:30; wherein the surface of the substrate to which the polymer/drug matrix coating is applied is covered by an impervious protective sheet; and wherein the supporting substrate is a composite material comprising a porous material laminated to a backing material which is impervious to the contents in the gel.

18. A pharmaceutical article according to claim 1, wherein the local anesthetic is lidocaine or procaine.

19. A pharmaceutical article for providing local anesthesia comprising:

(a) a substrate;

(b) an aqueous gel consisting essentially of a crosslinked copolymer of an alkyl (meth)acrylate and (meth)acrylic acid impregnated in the substrate; and (c) a local anesthetic dispersed in the gel.

20. The pharmaceutical article of claim 19, wherein at least 50% by weight of the alkyl (meth)acrylate units in the copolymer are alkyl (meth)acrylate units wherein the alkyl group has 1 to 3 carbon atoms.

21. The pharmaceutical article of claim 19, wherein the weight ratio of the alkyl (meth)acrylate units to (meth)acrylic acid units in the copolymer is 95:5 to 70:30.

22. The pharmaceutical article of claim 19, wherein the copolymer is a copolymer of an alkyl acrylate, a hydroxyalkyl acrylate and acrylic acid.

23. The pharmaceutical article of claim 19, wherein the local anesthetic content in the aqueous gel is 15 to 60% by weight based on the combined weight of the gel and anesthetic.

24. The pharmaceutical article of claim 19, wherein the local anesthetic is lidocaine or procaine.

25. The pharmaceutical article of claim 19, wherein the article further comprises a backing material impervious to the contents of the gel laminated to the substrate.

* * * * *